(12) United States Patent
Ikeda et al.

(10) Patent No.: US 6,207,184 B1
(45) Date of Patent: Mar. 27, 2001

(54) HYDROPHILIC ADHESIVE MASSES

(75) Inventors: Yasuo Ikeda, Narashino; Hirohisa Okuyama, Chiba-ken; Kenji Ishigaki, Chiba; Shuichi Kasai, Narita; Katsumi Imamori, Yotsukaido, all of (JP)

(73) Assignee: SSP Co., Ltd., Tokyo (JP)

( * ) Notice: Subject to any disclaimer, the term of this patent is extended or adjusted under 35 U.S.C. 154(b) by 0 days.

(21) Appl. No.: 09/330,065

(22) Filed: Jun. 11, 1999

(30) Foreign Application Priority Data

Jun. 18, 1998 (JP) .................................................. 10-171103

(51) Int. Cl.⁷ .............................. A61F 13/02; A61F 15/16
(52) U.S. Cl. .......................... 424/448; 424/446; 424/447; 424/443
(58) Field of Search .................................... 424/448, 446, 424/447, 443

(56) References Cited

U.S. PATENT DOCUMENTS 4,983,385 * 1/1991 Hasegawa et al. .................... 424/81
5,913,840 * 6/1999 Allenberg et al. ...................... 602/8

OTHER PUBLICATIONS

Patent Abstracts of Japan, vol. 13, No. 115 (C–578), Mar. 20, 1989, JP 63 290817, Nov. 28, 1988.
Patent Abstracts of Japan, vol. 16, No. 362 (C–0971), Aug. 5, 1992, JP 04 117323, Apr. 17, 1992.
Patent Abstracts of Japan, vol. 16, No. 362 (C–0971), Aug. 5, 1992, JP 04 117324, Apr. 17, 1992.
Choy Fun Wong, et al., International Journal of Pharmaceutics, vol. 178, No. 1, pp. 11–22, "Formulation and Evaluation of Controlled Release Eudragit Buccal Patches", Feb. 1, 1999.

* cited by examiner

Primary Examiner—Thurman K. Page
Assistant Examiner—Isis Ghali
(74) Attorney, Agent, or Firm—Oblon, Spivak, McClelland, Maier & Neustadt, P.C.

(57) ABSTRACT

A hydrophilic adhesive mass contains 0.05 to 10 wt. % of a copolymer of an aminoalkyl (meth)acrylate and an alkyl (meth)acrylate. This hydrophilic adhesive mass is excellent in adhesiveness, and especially when combined with a pharmacologically active ingredient, is suitable for use in providing hydrophilic plasters.

10 Claims, No Drawings

HYDROPHILIC ADHESIVE MASSES

BACKGROUND OF THE INVENTION a) Field of the Invention

This invention relates to hydrophilic adhesive masses and hydrophilic plasters, and specifically to hydrophilic adhesive masses, which are strong in adhesiveness and excellent in feeling of use, and also to hydrophilic plasters making use of the same.

b) Description of the Related Art

Hydrophilic plasters each of which carries a hydrophilic mass having adhesiveness and spread as an external preparation on a backing have been used for years. These hydrophilic plasters are required to remain in firm adherence to skin without peeling off during application.

Conventional plasters are known to include non-gelatin poultice composed of polyacrylic acid, a polyacrylate salt, carboxymethylcellulose and an alkali metal alginate (JP 59-110617 A); transdermal preparations composed of polyacrylic acid a 10% aqueous solution of which has a viscosity of from 100 to 1,000 cps, a water-soluble polymer, a polyhydric alcohol and water (JP 6-135828 A); water-containing gel plasters composed of an N-vinylacetamide-sodium acrylate copolymer, a water-soluble aluminum salt and water (JP 9-143060 A); and cataplasms added with polybutene and gelatin (JP 9-208462 A). They are however accompanied with one or more problems such as insufficient adhesiveness and/or difficulty in commercial production.

SUMMARY OF THE INVENTION

There is accordingly a long-standing desire for the provision of a hydrophilic adhesive mass having sufficient adhesiveness.

With the foregoing current circumstance in view, the present inventors have proceeded with extensive research. As a result, it has been found that a hydrophilic adhesive mass containing a copolymer of an aminoalkyl (meth) acrylate and an alkyl (meth)acrylate in a specific proportion has excellent adhesiveness to skin and also provides good feeling of use, leading to the completion of the present invention.

In one aspect of the present invention, there is thus provided a hydrophilic adhesive mass, which comprises 0.05 to 10 wt. % of a copolymer of an aminoalkyl (meth)acrylate and an alkyl (meth)acrylate.

In another aspect of the present invention, there is also provided a hydrophilic plaster comprising a backing and a paste formed of the above-described hydrophilic adhesive mass and at least one pharmacologically active ingredient and spread on the backing.

The hydrophilic adhesive mass and hydrophilic plaster according to the present invention have strong adhesiveness to skin and also provide good feeling of use.

DETAILED DESCRIPTION OF THE INVENTION AND PREFERRED EMBODIMENTS

No particular limitation is imposed on the aminoalkyl (meth)acrylate as one of the monomers making up the copolymer for use in the present invention. Nonetheless, one containing a tertiary amine or a quaternary ammonium salt as an amine moiety in its molecule can be mentioned as a preferred example. Examples of one containing a tertiary amine as an amine moiety in its molecule include dimethylaminoethyl (meth)acrylate, diethylaminoethyl (meth) acrylate, dibutylaminoethyl (meth)acrylate, morpholinoethyl (meth)acrylate, piperidinoethyl (meth)acrylate, dimethylamino-2-propyl (meth)acrylate, and dimethylaminoneopentyl (meth)acrylate.

On the other hand, examples of one containing a quaternary ammonium salt as an amine moiety in its molecule include trimethylammoniumethyl (meth)acrylate, triethylammoniumethyl (meth)acrylate, tributylammoniumethyl (meth)acrylate, trimorpholinoammoniumethyl (meth) acrylate, tripiperidinoammoniumethyl (meth)acrylate, trimethylammonium-2-propyl (meth)acrylate, and trimethylammoniumneopentyl (meth)acrylate. Incidentally, a tertiary amine moiety in a molecule can be converted with hydrochloric acid or the like into its corresponding quaternary ammonium salt moiety. As the aminoalkyl (meth)acrylate, dimethylaminoethyl (meth)acrylate or chlorinated trimethylammoniumethyl (meth)acrylate is particularly preferred.

No particular limitation is imposed on the alkyl (meth) acrylate as the other one of the monomers making up the copolymer. However, preferred examples include methyl (meth)acrylate, ethyl (meth)acrylate, n-butyl (meth) acrylate, n-hexyl (meth)acrylate, n-octyl (meth)acrylate, 2-ethylhexyl (meth)acrylate, and n-dodecyl (meth)acrylate. They may be used either singly or in combination. In particular, methyl (meth)acrylate, ethyl (meth)acrylate and n-butyl (meth)acrylate are suitably usable.

The copolymer may have any one of random, alternating, block and graft structures, but a block copolymer is preferred.

Examples of the copolymer, which are particularly preferred for use in the present invention, include a block copolymer of dimethylaminoethyl (meth)acrylate, methyl (meth)acrylate and butyl (meth)acrylate; and a block copolymer of chlorinated trimethylammoniumethyl (meth)acrylate, methyl (meth)acrylate and ethyl (meth)acrylate.

As the copolymer for use in the present invention, a commercial product may be employed. Illustrative of such a commercial product are "EUDRAGIT RL 12,5", "EUDRAGIT RL 100", "EUDRAGIT RL PO,", "EUDRAGIT RL 30 D", "EUDRAGIT RS 12,5", "EUDRAGIT RS 100", "EUDRAGIT RS PO,", "EUDRAGIT RS 30 D", "EUDRAGIT E 12,5", "EUDRAGIT E 100", "PLASTOID E 35 L", "PLASTOID E 35 M", "PLASTOID E 35 H" and "PLASTOID L 50" (all, products of Röhm AG).

The proportion of the copolymer employed in the present invention may preferably be set at 0.05 to 10 wt. % based on the whole weight of the hydrophilic adhesive mass, with 0.1 to 6 wt. %, further 0.2 to 4 wt. % being especially preferred. A proportion smaller than 0.05 wt. % makes it difficult to obtain high adhesiveness, while a proportion greater than 10 wt. % cannot bring about extra adhesiveness improving effect and hence, is not economical.

The adhesiveness of the hydrophilic adhesive mass of the present invention can be improved further by incorporating a hydrophilic adhesive in addition to the above-described copolymer. Illustrative of such an hydrophilic adhesive are polyacrylic acids and salts thereof such as polyacrylic acid, sodium polyacrylate, crosslinked branched polyacrylic acid, crosslinked branched sodium polyacrylate, potassium polyacrylate, monoethanolamine polyacrylate, diethanolamine polyacrylate, triethanolamine polyacrylate, and ammonium polyacrylate; copolymers each obtained using acrylic acid or a salt thereof as one of its components, such as starch grafted acrylate, and N-vinylacetamide-sodium acrylate copolymer; cellulose derivatives and salts thereof, such as hydroxyethylcellulose, hydroxypropylcellulose, hydroxypropylmethylcellulose, hydrophobized hydroxypropylmethylcellulose, methylcellulose, and carboxymethylcellulose sodium; polyvinyl alcohol; polyvinylpyrrolidone; polyethylene oxide; methoxyethylene maleic anhydride copolymer; polyacrylamide; alginic acid; sodium alginate; propylene glycol alginate; gelatin; acacia; tragacanth gum; locust bean gum; guar gum; tamarind gum; xanthan gum; gellan gum; carrageenan; and agar. Among these, particularly preferred are polyacrylic acid, sodium polyacrylate, crosslinked branched polyacrylic acid, crosslinked branched sodium polyacrylate, starch grafted acrylate, N-vinylacetamide-sodium acrylate copolymer, hydroxyethylcellulose, hydroxypropylcellulose, hydroxypropylmethylcellulose, hydrophobized hydroxypropylmethylcellulose, and carboxymethylcellulose sodium. These hydrophilic adhesives may be used either singly or in combination. Their proportion may preferably range from 0.5 to 50 wt. % based on the whole weight of the mass, with 2 to 40 wt. %, further 3 to 30 wt. % being particularly preferred.

In the present invention, use of a copolymer solubilizer is also preferred to dissolve the copolymer of the aminoalkyl (meth)acrylate and the alkyl (meth)acrylate. No particular limitation is imposed on such a copolymer solubilizer insofar as it can dissolve the copolymer and is pharmaceutically acceptable. It is possible to use, for example, one or more substances selected from polyhydric alcohols, fatty acid esters, surfactants, fatty acids, alcohols and hydrocarbons. Specific examples includes, as polyhydric alcohols, 1,3-butylene glycol, propylene glycol and dipropylene glycol; as fatty acid esters, dibutyl adipate, diisopropyl adipate, diethyl sebacate, diisopropyl sebacate, isopropyl myristate, isopropyl palmitate, cetyl lactate, myristyl lactate, ethyl linoleate, isopropyl linoleate, propylene glycol oleate, propylene glycol monocaprylate, propylene glycol dicaprylate, and propylene glycol didecanoate; as surfactants, polyoxyethylene lauryl ether, polyoxyethylene cetyl ether, polyoxyethylene oleyl ether, and lauryl diethanolamide; as fatty acids, lactic acid, lauric acid, oleic acid, linolic acid and linoleic acid; and as alcohols, ethanol, isopropyl alcohol, lauryl alcohol, oleyl alcohol, benzyl alcohol, phenethyl alcohol, and menthol; and as hydrocarbons, liquid paraffin and squalane. To the hydrophilic adhesive mass, these copolymer solubilizers may be added preferably in an proportion of from 0.5 to 70 wt. %, with 1 to 60 wt. %, further 5 to 50 wt. % being particularly preferred.

To the hydrophilic adhesive mass according to the present invention, skin penetration enhancers, crosslinking agents and humectants can be added further. They may be added either singly or in combination.

Examples of skin penetration enhancers for enhancing skin penetration of active ingredient(s) include known skin penetration enhancers such as fatty acids, fatty acid esters, polyhydric alcohols, alcohols, surfactants, organic bases, organic acids, vitamins and lecithin.

No particular limitation is imposed on the kind of a crosslinking agent insofar as it can crosslink the hydrophilic adhesive. Specifically, however, multi-valent metal compounds are preferred. As such multi-valent metal compounds, aluminum compounds, magnesium compounds and calcium compounds are particularly preferred.

Illustrative aluminum compounds, magnesium compounds and calcium compounds include aluminum potassium sulfate, aluminum ammonium sulfate, aluminum hydroxide, aluminum sulfate, aluminum chloride, aluminum glycinate, aluminum acetoglutamide, aluminum acetate, aluminum oxide, synthetic aluminum silicate, aluminometasilicate, calcium hydroxide, calcium carbonate, calcium sulfate, calcium nitrate, calcium chloride, calcium acetate, calcium oxide, calcium phosphate, magnesium hydroxide, magnesium carbonate, magnesium sulfate, magnesium acetate, magnesium silicate, magnesium oxide, magnesium hydroxide-aluminum hydroxide co-precipitate, magnesium aluminometasilicate, magnesium aluminosilicate, and synthetic hydrotalcite; and hydrates and anhydrides of these compounds. These compounds may be used either singly or in combination. The proportion of the crosslinking agent may desirably range from 0.001 to 10 wt. %, preferably from 0.01 to 5 wt. %, more preferably from 0.1 to 2 wt. %, although it varies depending on its kind as a compound.

No particular limitation is imposed on the humectant insofar as it is generally employed. Illustrative of the humectant are concentrated glycerin, xylitol, sorbitol, maltitol, pyrrolidonecarboxylic acid, sodium pyrrolidonecarboxylate, sodium lactate, hyaluronic acid, sodium hyaluronate, and urea. Its proportion may be set preferably at 5 to 40 wt. %.

Desirably, the hydrophilic adhesive mass according to the present invention may contain water in a proportion of from 1 to 85 wt. %, preferably from 5 to 70 wt. %, more preferably from 15 to 60 wt. %.

The hydrophilic adhesive mass may be used as is without specifically adding a pharmacologically active ingredient, for example, as a paste for cooling the local fever or as a supporter for compresses. As an alternative, one or more pharmacologically active ingredients may be added to the hydrophilic adhesive mass to provide a hydrophilic plaster. The following drugs can be mentioned as examples of pharmacologically active ingredients usable upon production of hydrophilic plasters.

Analgesic antiphlogistics: as non-steroidal analgesic antiphlogistics, glycol salicylate, methyl salicylate, alclofenac, anfenac sodium, ufenamate, suprofen, bufexamac, ampiroxicam, piroxicam, meloxicam, indomethacin, ketoprofen, zaltoprofen, sulindac, tenoxicam, acetaminophen, mefenamic acid, flufenamic acid, ibuprofen, loxoprofen, pranoprofen, fenbufen, diclofenac, diclofenac sodium, oxyphenbutazone, felbinac, and flurbiprofen; and as steroidal analgesic antiphlogistics, amcinonide, prednisolone valerate acetate, diflucortolone valerate, dexamethasone valerate, betamethasone valerate, diflorasone acetate, dexamethasone acetate, hydrocortisone acetate, methylprednisolone acetate, difluprednate, betamethasone dipropionate, dexamethasone, triamcinolone acetonide, halcinonide, flumethasone pivalate, budesonide, mometasone furancarboxylate, fluocinonide, fluocinolone acetonide, fludroxycortide, prednisolone, alclometasone propionate, clobetasol propionate, dexamethasone propionate, deprodone propionate, belcomethasone propionate, betamethasone, clobetasone butyrate, hydrocortisone butyrate, hydrocortisone butyrate propionate, and betamethasone butyrate propionate.

Antifungal agents: croconazole hydrochloride, neticonazole hydrochloride, clotrimazole, ketoconazole, isoconazole nitrate, econazole nitrate, oxiconazole nitrate, sulconazole nitrate, miconazole nitrate, tioconazole, bifonazole, and lanoconazole.

Drugs for urinary incontinence: oxybutynin hydrochloride, terodiline hydrochloride, and flavoxate hydrochloride.

Skeletal muscular relaxants: eperisone hydrochloride, afloqualone, chlorphenesin carbamate, tizanidine hydrochloride, tolperisone hydrochloride, oxazolam, flurazepam hydrochloride, diazepam, prazepam, flunitrazepam, flurazepam, brotizolam, bromazepam, chlorzoxazone, phenprobamate, methocarbamol, dantrolene sodium, and pridinol mesilate.

Antispasmodics: scopolamine butylbromide, atropine sulfate, papaverine hydrochloride.

Cardiacs: nitroglycerin, and isosorbide nitrate.

Smoking cessation aid: nicotine.

Antiallergic agents: azelastine hydrochloride, epinastine hydrochloride, oxatomide, seratrodast, tranilast, and ketotifen fumarate.

Topical anesthetics: procaine hydrochloride, dibucaine hydrochloride, and lidocaine.

Antiseptic disinfectants: iodine, iodine tincture, iodoform, and povidone-iodine.

Skin irritants: capsaicin, capsicum extract, and 4-hydroxy-3-methoxybenzyl nonylic acid amide.

It is to be noted that the pharmacologically active ingredient for use in the hydrophilic plaster according to the present invention is not limited to the above-exemplified ones. These pharmacologically active ingredients can be used either singly or in combination as needed.

In the hydrophilic adhesive mass according to the present invention and the paste for use in the hydrophilic adhesive mass according to the present invention, said hydrophilic adhesive mass and paste being hereinafter to be collectively called "the hydrophilic adhesive mass", additives which are generally added to hydrophilic adhesive masses and the like can be incorporated. For example, it is possible to add, as crosslinking rate regulators, chelating agents such as sodium edetate and sodium metaphosphate, organic acids such as lactic acid, citric acid and tartaric acid, metal salts of such organic acids, inorganic acids such as sulfuric acid and hydrochloric acid, organic bases such as diethylamine, diethanolamine, triethanolamine and diisopropanolamine, inorganic bases such as sodium hydroxide and ammonia; as fillers, kaolin, titanium dioxide, light silicic anhydride and hydrophobic light silicic anhydride; as antioxidants, sulfites such as anhydrous sodium sulfite, sodium hydrogensulfite, sodium pyrrosulfite, rongalite, sodium edetate, dibutylhydroxytoluene and dibutylhydroxyanisole. In addition, surfactants, perfumes, preservatives, pH regulators and the like can also be incorporated as needed.

No particular limitation is imposed on the production process of the hydrophilic adhesive mass according to the present invention, and a production process for conventional hydrophilic adhesive masses or hydrophilic plasters can be employed. In the case of the hydrophilic plaster according to the present invention, for example, the above-described essential ingredients and if necessary, other ingredients are mixed in water, followed by thorough kneading until a uniform paste is formed. The paste is spread on a backing such as a paper sheet, woven cloth, non-woven cloth or plastic film and, if necessary, is then covered with a polyethylene film or the like.

The present invention will next be described by examples. It is however to be noted that the present invention is by no means limited to them.

EXAMPLE 1

Hydrophilic plasters which carried hydrophilic adhesive masses of the compositions presented in Table 1 were produced by the following production process.

(Production Process)

(A) Polyoxyethylene (9) lauryl ether and a portion of propylene glycol were combined into an intimate mixture, and diclofenac sodium, "EUDRAGIT RL PO" and L-menthol were added to and dissolved in the mixture. (B) Kaolin and sodium edetate were added to and dispersed in a liquid mixture of purified water and a D-sorbitol solution (70%). (C) In a liquid mixture of the remaining portion of the propylene glycol and concentrated glycerin, sodium polyacrylate, carboxymethylcellulose sodium and dried aluminum potassium sulfate were evenly dispersed. The solution (A) and the dispersions (B) (C) so obtained were charged in a kneader and were then agitated there. Tartaric acid was added further, and the resulting mixture was thoroughly stirred until a uniform paste was formed, whereby a hydrophilic adhesive mass was prepared. The mass was evenly spread on a non-woven cloth, so that a hydrophilic plaster with the hydrophilic adhesive mass carried thereon was produced.

Test 1

An organoleptic human-skin adhesiveness test was performed by applying the above-produced hydrophilic plasters to the elbows of volunteers.

(Testing Method)

Samples of each plaster so produced were applied to the elbows of 20 volunteers, respectively, and upon elapsed time of 8 hours, the plaster samples were peeled off. The degree of adhesiveness was ranked by the following ranking system. The results are also presented in Table 1.

Ranking System (Organoleptic Human-Skin Adhesiveness Test)

A: strong (remains firmly adhering during test).

B: slightly weak (partial peeling takes place during test).

C: weak (falls off during test).

TABLE 1

| Component (wt. %) | Invention Product | | | | | | | | | | Comparative Product | | |
| --- | --- | --- | --- | --- | --- | --- | --- | --- | --- | --- | --- | --- | --- |
| | 1 | 2 | 3 | 4 | 5 | 6 | 7 | 8 | 9 | 10 | 1 | 2 | 3 |
| Diclofenac sodium | 1.00 | 1.00 | 1.00 | 1.00 | 1.00 | 1.00 | 1.00 | 1.00 | 1.00 | 1.00 | 1.00 | 1.00 | 1.00 |
| Polyoxyethylene (9) lauryl ether | 1.00 | 1.00 | 1.00 | 1.00 | 1.00 | 1.00 | 1.00 | 1.00 | 1.00 | 1.00 | 1.00 | 1.00 | 1.00 |
| L-menthol | 0.50 | 0.50 | 0.50 | 0.50 | 0.50 | 0.50 | 0.50 | 0.50 | 0.50 | 0.50 | 0.50 | 0.50 | 0.50 |
| Propylene glycol | 5.00 | 5.00 | 5.00 | 5.00 | 5.00 | 5.00 | 5.00 | 5.00 | 5.00 | 5.00 | 5.00 | 5.00 | 5.00 |
| Concentrated Glycerin | 15.00 | 15.00 | 15.00 | 15.00 | 15.00 | 15.00 | 15.00 | 15.00 | 15.00 | 15.00 | 15.00 | 15.00 | 15.00 |
| D-sorbitol solution (70%) | 30.00 | 30.00 | 30.00 | 30.00 | 30.00 | 30.00 | 30.00 | 30.00 | 30.00 | 30.00 | 30.00 | 30.00 | 30.00 |
| Sodium polyacrylate | 5.00 | 5.00 | 5.00 | 5.00 | 5.00 | 5.00 | 5.00 | 5.00 | 5.00 | 5.00 | 5.00 | 5.00 | 5.00 |
| Carboxymethylcellulose sodium | 2.00 | 2.00 | 2.00 | 2.00 | 2.00 | 2.00 | 2.00 | 2.00 | 2.00 | 2.00 | 2.00 | 2.00 | 2.00 |
| EUDRAGIT RL PO | 0.05 | 0.10 | 0.20 | 0.50 | 1.00 | 2.00 | 3.00 | 4.00 | 5.00 | 6.00 | | 0.01 | 0.04 |
| Kaolin | 3.00 | 3.00 | 3.00 | 3.00 | 3.00 | 3.00 | 3.00 | 3.00 | 3.00 | 3.00 | 3.00 | 3.00 | 3.00 |
| Sodium edetate | 0.05 | 0.05 | 0.05 | 0.05 | 0.05 | 0.05 | 0.05 | 0.05 | 0.05 | 0.05 | 0.05 | 0.05 | 0.05 |
| Dried aluminum potassium sulfate | 0.50 | 0.50 | 0.50 | 0.50 | 0.50 | 0.50 | 0.50 | 0.50 | 0.50 | 0.50 | 0.50 | 0.50 | 0.50 |

TABLE 1-continued

|  | Invention Product | | | | | | | | | | Comparative Product | | |
|---|---|---|---|---|---|---|---|---|---|---|---|---|---|
| Component (wt. %) | 1 | 2 | 3 | 4 | 5 | 6 | 7 | 8 | 9 | 10 | 1 | 2 | 3 |
| Tartaric acid | 0.10 | 0.10 | 0.10 | 0.10 | 0.10 | 0.10 | 0.10 | 0.10 | 0.10 | 0.10 | 0.10 | 0.10 | 0.10 |
| Purified water | 36.80 | 36.75 | 36.65 | 36.35 | 35.85 | 34.85 | 33.85 | 32.85 | 31.85 | 30.85 | 36.85 | 36.84 | 36.81 |
| Total (wt. %) | 100.00 | 100.00 | 100.00 | 100.00 | 100.00 | 100.00 | 100.00 | 100.00 | 100.00 | 100.00 | 100.00 | 100.00 | 100.00 |
| Organoleptic human-skin adhesiveness test | A | A | A | A | A | A | A | A | A | A | C | C | B |

As is evident from the results of Test 1 as presented in Table 1, the hydrophilic plasters of the present invention (the invention products 1–10) with the hydrophilic adhesive masses according to the present invention, different from the comparative products 1–3, retained strong adhesiveness to the human skin over a predetermined time. The comparative products either fell off or partly peeled in the predetermined time, and failed to provide strong adhesiveness.

EXAMPLE 2

Hydrophilic plasters with the hydrophilic adhesive masses presented in Table 2 were produced in the same manner as the invention products 1–6 in Example 1 except that "EUDRAGIT RL PO" was changed to "EUDRAGIT E 100". An organoleptic human-skin adhesiveness test was also performed in the same manner as in Test 1. The test results are also presented in Table 2.

TABLE 2

|  | Invention Product | | | | | | Comp. Product |
|---|---|---|---|---|---|---|---|
| Component (wt. %) | 11 | 12 | 13 | 14 | 15 | 16 | 4 |
| Diclofenac sodium | 1.00 | 1.00 | 1.00 | 1.00 | 1.00 | 1.00 | 1.00 |
| Polyoxyethylene (9) lauryl ether | 1.00 | 1.00 | 1.00 | 1.00 | 1.00 | 1.00 | 1.00 |
| L-menthol | 0.50 | 0.50 | 0.50 | 0.50 | 0.50 | 0.50 | 0.50 |
| Propylene glycol | 5.00 | 5.00 | 5.00 | 5.00 | 5.00 | 5.00 | 5.00 |
| Concentrated Glycerin | 15.00 | 15.00 | 15.00 | 15.00 | 15.00 | 15.00 | 15.00 |
| D-sorbitol solution (70%) | 30.00 | 30.00 | 30.00 | 30.00 | 30.00 | 30.00 | 30.00 |
| Sodium polyacrylate | 5.00 | 5.00 | 5.00 | 5.00 | 5.00 | 5.00 | 5.00 |
| Carboxymethylcellulose sodium | 2.00 | 2.00 | 2.00 | 2.00 | 2.00 | 2.00 | 2.00 |
| EUDRAGIT E 100 | 0.05 | 0.10 | 0.20 | 0.50 | 1.00 | 2.00 |  |
| Kaolin | 3.00 | 3.00 | 3.00 | 3.00 | 3.00 | 3.00 | 3.00 |
| Sodium edetate | 0.05 | 0.05 | 0.05 | 0.05 | 0.05 | 0.05 | 0.05 |
| Dried aluminum potassium sulfate | 0.50 | 0.50 | 0.50 | 0.50 | 0.50 | 0.50 | 0.50 |
| Tartaric acid | 0.10 | 0.10 | 0.10 | 0.10 | 0.10 | 0.10 | 0.10 |
| Purified water | 36.80 | 36.75 | 36.65 | 36.35 | 35.85 | 34.85 | 36.85 |
| Total (wt. %) | 100.00 | 100.00 | 100.00 | 100.00 | 100.00 | 100.00 | 100.00 |
| Organoleptic human-skin adhesiveness test | A | A | A | A | A | A | C |

The hydrophilic plasters of the present invention (the invention products 11–16) with the hydrophilic adhesive masses according to the present invention exhibited strong adhesiveness.

EXAMPLE 3

Hydrophilic plasters with hydrophilic adhesive masses the compositions of which are presented in Table 3 and Table 4 were produced.

TABLE 3

| Component | Invention Product | | | | | |
|---|---|---|---|---|---|---|
| (wt. %) | 17 | 18 | 19 | 20 | 21 | 22 |
| Diclofenac sodium | 1.00 | 1.00 | 1.00 |  |  |  |
| Piroxicam |  |  |  | 0.50 |  |  |
| Meloxicam |  |  |  |  | 0.50 |  |
| Neticonazole hydrochloride |  |  |  |  |  | 1.00 |
| Oxybutynin hydrochloride |  |  |  |  |  |  |
| Eperisone hydrochloride |  |  |  |  |  |  |
| Nitroglycerin |  |  |  |  |  |  |
| Nicotine |  |  |  |  |  |  |

TABLE 3-continued

| Component | Invention Product | | | | | |
|---|---|---|---|---|---|---|
| (wt. %) | 17 | 18 | 19 | 20 | 21 | 22 |
| Oxatomide |  |  |  |  |  |  |
| Lidocaine |  |  |  |  |  |  |
| Diisopropyl adipate | 2.50 |  |  |  |  |  |
| Diethyl sebacate |  |  | 1.00 |  |  |  |
| Diisopropyl |  | 4.00 |  |  |  |  |

TABLE 3-continued

| Component (wt. %) | Invention Product | | | | | |
|---|---|---|---|---|---|---|
| | 17 | 18 | 19 | 20 | 21 | 22 |
| sebacate | | | | | | |
| Polyoxyethylene (9) lauryl ether | 1.00 | | | 1.00 | 5.00 | 2.50 |
| Polyoxyethylene (10) oleyl ether | | 5.00 | | | | |
| Myristyl lactate | | | | 5.00 | | |
| Oleic acid | | | | | | 2.50 |
| Benzyl alcohol | | | | | 5.00 | |
| Squalane | | | | | | |
| L-menthol | | 1.00 | 0.50 | 0.50 | 0.50 | |
| Propylene glycol | 10.00 | 40.00 | 10.00 | | 10.00 | |
| Concentrated Glycerin | | 20.00 | 15.00 | 20.00 | 20.00 | 25.00 |
| D-sorbitol solution (70%) | | | 20.00 | 20.00 | | 30.00 |
| Polyacrylic acid | | | 1.00 | | | 1.00 |
| Sodium polyacrylate | 3.00 | | 5.00 | 5.00 | 5.00 | 5.00 |
| Crosslinked branched polyacrylic acid | 4.00 | | | | | 0.20 |
| N-vinylacetamide/sodium acrylate copolymer | | 3.00 | | | | |
| Hydroxypropylcellulose | | | | 1.00 | | 0.50 |
| Hydrophobized Hydroxypropylmethylcellulose | | | 1.00 | | | |
| Carboxymethylcellulose sodium | | | 3.00 | 1.00 | | 2.00 |
| Polyvinylpyrrolidone | | | | | | |
| EUDRAGIT RL PO | | 1.00 | | | | |
| EUDRAGIT E 100 | 1.00 | | 0.10 | 0.50 | 1.00 | 0.20 |
| Kaolin | | | 5.00 | 5.00 | 3.00 | |
| Light anhydrous silicic acid | | 2.00 | | | 2.00 | |
| Sodium edetate | 0.15 | | 0.05 | 0.05 | 0.05 | 0.05 |
| Dried aluminum potassium sulfate | 0.35 | 0.30 | | | 0.45 | |
| Aluminum glycinate | | | 0.25 | | | 0.01 |
| Synthetic hydroxytalcite | | | | 2.00 | | |
| Tartaric acid | | 0.01 | 0.10 | 0.30 | 0.30 | 2.00 |
| Triethanolamine | 7.00 | | | | | |
| Purified water | 70.00 | 22.69 | 60.00 | 36.15 | 26.20 | 28.94 |
| Total (wt. %) | 100.00 | 100.00 | 100.00 | 100.00 | 100.00 | 100.00 |
| Mass weight (g/m$^2$) | 1000 | 200 | 1000 | 1000 | 1000 | 200 |

TABLE 4

| Component (wt. %) | Invention Product | | | | | |
|---|---|---|---|---|---|---|
| | 23 | 24 | 25 | 26 | 27 | 28 |
| Diclofenac sodium | | | | | | |
| Piroxicam | | | | | | |
| Meloxicam | | | | | | |
| Neticonazole hydrochloride | 1.50 | | | | | |
| Oxybutynin hydrochloride | | | | | | |
| Eperisone hydrochloride | | 0.50 | | | | |
| Nitroglycerin | | | 0.10 | | | |
| Nicotine | | | | 0.10 | | |
| Oxatomide | | | | | 2.00 | |
| Lidocaine | | | | | | 2.00 |
| Diisopropyl adipate | 5.00 | | | | 5.00 | 2.50 |
| Diethyl sebacate | | | | | | |
| Diisopropyl sebacate | | | | | | |
| Polyoxyethylene (9) lauryl ether | 5.00 | | 1.00 | 0.50 | 5.00 | 2.50 |
| Polyoxyethylene (10) oleyl ether | | 5.00 | | | | |
| Myristyl lactate | | | | | | |
| Oleic acid | | | | | | |
| Benzyl alcohol | | | | | | |
| Squalane | | 5.00 | | | | |
| L-menthol | 0.50 | | | | | |
| Propylene glycol | 40.00 | 10.00 | 20.00 | | 10.00 | 40.00 |
| Concentrated Glycerin | 25.00 | 10.00 | 40.00 | 20.00 | 20.00 | 15.00 |
| D-sorbitol solution (70%) | | 20.00 | | 30.00 | 20.00 | |
| Polyacrylic acid | | | 20.00 | | | 10.00 |
| Sodium polyacrylate | | 5.00 | | 5.00 | 5.00 | |
| Crosslinked branched polyacrylic acid | | | | | | |
| N-vinylacetamide/sodium acrylate copolymer | 2.50 | | | | | |
| Hydroxypropylcellulose | | | | | | |
| Hydrophobized hydroxypropylmethylcellulose | | | | | | |
| Carboxymethylcellulose sodium | | 2.00 | | 3.00 | 2.00 | 3.00 |
| Polyvinylpyrrolidone | 0.20 | | 5.00 | | | 4.00 |
| EUDRAGIT RL PO | 2.00 | | | | | 4.00 |
| EUDRAGIT E 100 | | 1.00 | 3.00 | 0.10 | 0.50 | |
| Kaolin | | 2.00 | | 1.00 | 5.00 | |
| Light anhydrous silicic acid | 3.00 | 2.00 | 5.00 | 3.00 | 3.00 | |
| Sodium edetate | 0.05 | 0.10 | 0.05 | 0.15 | 0.12 | 0.10 |
| Dried aluminum potassium sulfate | | 0.35 | 0.45 | 0.40 | 0.09 | 0.50 |
| Aluminum glycinate | 0.15 | | | | | |

TABLE 4-continued

| Component (wt. %) | Invention Product | | | | | |
|---|---|---|---|---|---|---|
| | 23 | 24 | 25 | 26 | 27 | 28 |
| Synthetic hydroxytalcite | | | | | | |
| Tartaric acid | 0.10 | 0.20 | | 1.00 | 1.20 | 1.20 |
| Triethanol-amine | | | 0.40 | | | |
| Purified water | 15.00 | 36.85 | 5.00 | 35.75 | 21.09 | 15.20 |
| Total (wt. %) | 100.00 | 100.00 | 100.00 | 100.00 | 100.00 | 100.00 |
| Mass weight (g/m$^2$) | 200 | 1000 | 200 | 1000 | 200 | 1000 |

What is claimed is:

1. A hydrophilic plaster comprising a backing; and a paste formed of a hydrophilic adhesive mass, comprising 0.05 to 10 wt. % of a copolymer of an aminoalkyl (meth)acrylate and an alkyl (meth)acrylate and a cross linking agent selected from the group consisting of aluminum compounds, magnesium compounds and calcium compounds, and spread on said backing.

2. The hydrophilic plaster according to claim 1, wherein an amine moiety in said aminoalkyl (meth)acrylate has been obtained from a tertiary amine or a quaternary ammonium salt.

3. The hydrophilic plaster according to claim 1, wherein an amine moiety in said aminoalkyl (meth)acrylate has been obtained from dimethylamine or trimethylammonium chloride.

4. The hydrophilic plaster according to claim 1, further comprising at least one hydrophilic adhesive selected from the group consisting of polyacrylic acid and salts thereof, copolymers obtained using acrylic acid or salts thereof, and cellulose derivatives and salts thereof.

5. The hydrophilic plaster according to claim 4, wherein said at least one hydrophilic adhesive is selected from the group consisting of polyacrylic acid, sodium polyacrylate, crosslinked branched polyacrylic acid, crosslinked branched sodium polyacrylate, crosslinked product of acrylic acid-starch graft copolymer, N-vinylacetamide-sodium acrylate copolymer, hydroxyethylcellulose, hydroxypropylcellulose, hydroxypropylmethylcellulose, hydrophobized hydroxypropylmethylcellulose, and carboxymethylcellulose sodium.

6. The hydrophilic plaster according to claim 1, further comprising, as a solubilizer for said copolymer of said aminoalkyl (meth)acrylate and said alkyl (meth)acrylate, at least one ingredient selected from the group consisting of polyhydric alcohols, fatty acid esters, surfactants, fatty acids, alcohols and hydrocarbons.

7. The hydrophilic plaster according to claim 1, wherein water is contained in a proportion of from 1 to 85 wt. %.

8. The hydrophilic plaster according to claim 1, further comprising at least one ingredient selected from the group consisting of skin penetration enhancers and humectants.

9. The hydrophilic plaster according to claim 1, wherein the paste additionally contains at least one pharmacologically active ingredient.

10. The hydrophilic plaster according to claim 9, wherein said at least one pharmacologically active ingredient is selected from the group consisting of analgesic antiphlogistics, antifungal agents, drugs for urinary incontinence, skeletal muscular relaxants, antispasmodics, cardiacs, smoking cessation aids, antiallergic drugs, topical anesthetics, antiseptic disinfectants and skin irritants.

* * * * *